(12) United States Patent
Furuta et al.

(10) Patent No.: US 10,047,029 B2
(45) Date of Patent: Aug. 14, 2018

(54) PROCESS FOR PRODUCING ALKYLENE OXIDE ADDUCT AND ALKYLENE OXIDE ADDUCT

(71) Applicant: Takemoto Yushi Kabushiki Kaisha, Gamagori-shi, Aichi-ken (JP)

(72) Inventors: Akihiro Furuta, Gamagori (JP); Kazuhisa Okada, Gamagori (JP)

(73) Assignee: TAKEMOTO YUSHI KABUSHIKI KAISHA, Gamagori Shi, Aichi-Ken (JP)

(*) Notice: Subject to any disclaimer, the term of this patent is extended or adjusted under 35 U.S.C. 154(b) by 0 days.

(21) Appl. No.: 15/117,683

(22) PCT Filed: Mar. 10, 2014

(86) PCT No.: PCT/JP2014/056154
§ 371 (c)(1),
(2) Date: Aug. 9, 2016

(87) PCT Pub. No.: WO2015/136596
PCT Pub. Date: Sep. 17, 2015

(65) Prior Publication Data
US 2016/0368847 A1 Dec. 22, 2016

(51) Int. Cl.
C07C 41/03 (2006.01)
C07C 43/13 (2006.01)
C07C 213/04 (2006.01)
C08G 65/26 (2006.01)
B01J 19/00 (2006.01)

(52) U.S. Cl.
CPC ........... *C07C 41/03* (2013.01); *B01J 19/0093* (2013.01); *C07C 43/13* (2013.01); *C07C 213/04* (2013.01); *C08G 65/26* (2013.01); *C08G 65/2609* (2013.01); *C08G 65/2621* (2013.01); *C08G 65/2696* (2013.01)

(58) Field of Classification Search
None
See application file for complete search history.

(56) References Cited

U.S. PATENT DOCUMENTS

| | | | |
|---|---|---|---|
| 2005/0245628 A1 | 11/2005 | Hubel et al. | |
| 2009/0203874 A1* | 8/2009 | Loffler | C08G 18/4866 528/405 |
| 2010/0041923 A1 | 2/2010 | Franzen et al. | |
| 2011/0118469 A1* | 5/2011 | Bedore | B01J 19/0093 546/157 |
| 2013/0131389 A1* | 5/2013 | Loeffler | C08G 65/2696 568/623 |

FOREIGN PATENT DOCUMENTS

| | | |
|---|---|---|
| JP | 52-151108 | 12/1977 |
| JP | 53-090208 | 8/1978 |
| JP | 07-048305 | 2/1995 |
| JP | 2008-050293 | 3/2008 |
| JP | 2008-120737 | 5/2008 |
| JP | 2009-537687 | 10/2009 |
| JP | 2010-138388 | 6/2010 |
| JP | 2014-084443 | 5/2014 |
| WO | 01/36514 A | 5/2001 |

OTHER PUBLICATIONS

WO patent application No. PCT/JP2014/056154, International Search Report dated May 27, 2014.
Supplemental European Search Report, dated Sep. 29, 2017, for European Patent Application No. 14885564.6.

* cited by examiner

*Primary Examiner* — Rosalynd A Keys
(74) *Attorney, Agent, or Firm* — Weaver Austin Villeneuve & Sampson, LLP

(57) ABSTRACT

A process for producing an alkylene oxide adduct can continuously produce the alkylene oxide adduct by using a microflow reactor having a tubular flow passage and a micromixer connected to a supply port of the microflow reactor. Liquid state alkylene oxide, alkylene catalyst and an organic compound having an active hydrogen atom(s) are reacted while passing therethrough under the conditions of a temperature of the flow passage of 70 to 200° C. and a pressure of the supply port of the flow passage of 1 to 10 MPa.

5 Claims, No Drawings

PROCESS FOR PRODUCING ALKYLENE OXIDE ADDUCT AND ALKYLENE OXIDE ADDUCT

TECHNICAL FIELD

The present invention relates to a process for producing an alkylene oxide adduct and the alkylene oxide adduct, more specifically to a process for producing an alkylene oxide adduct using a microflow reactor having a tubular flow passage and the alkylene oxide adduct obtained by such a process.

BACKGROUND ART

An alkylene oxide adduct has heretofore generally been produced by a batch-type reaction method. The batch-type reaction method is a method for producing an alkylene oxide adduct by charging an organic compound having an active hydrogen atom(s) as a starting material and a catalyst in an autoclave, and after injecting an alkylene oxide, reacting these materials under pressure at a predetermined temperature (for example, see Patent Documents 1 to 3). However, in the method for producing the alkylene oxide adduct by such a batch-type reaction method involves the problems that 1) the alkylene oxide adduct cannot be produced continuously, 2) there is a risk of explosion since the addition reaction is carried out in a large-sized apparatus, 3) a temperature or a pressure at the time of the addition reaction is difficultly controlled since the reaction is carried out by the gas-liquid reaction, so that quality of the product is lowered that coloring is generated and the molecular weight distribution is broadened, etc., and 4) the producing apparatus is expensive, etc. As an improving method of such a batch-type reaction method, a continuous reaction method using a tube reactor (for example, see Patent Documents 4 and 5) has been proposed, but the method for producing the alkylene oxide adduct by such a conventional continuous reaction method involves the problems that 1) a temperature or a pressure at the time of the addition reaction is still difficultly controlled, so that quality of the product is lowered that coloring is generated and the molecular weight distribution is broadened, etc., and 2) mass production is difficult, etc.

PRIOR ART DOCUMENTS

Patent Documents

Patent Document 1: JP Hei.7-48305A
Patent Document 2: JP 2008-50293A
Patent Document 3: JP 2008-120737A
Patent Document 4: JP Sho.52-151108A
Patent Document 5: JP Sho.53-90208A

SUMMARY OF THE INVENTION

Problems to be Solved by the Invention

A problem to be solved by the present invention is that an alkylene oxide adduct can be continuously produced with an optional size from a small size to a large size, a temperature and a pressure at the time of the addition reaction can be controlled with high precision, and as a result, an alkylene oxide adduct with high quality having no coloring and narrow molecular weight distribution can be continuously produced, and an object thereof is to provide a process for producing the alkylene oxide adduct which can accomplish the above simultaneously and such an alkylene oxide adduct.

Means to Solve the Problems

The present inventors have studied to solve the above-mentioned problems, and as a result, they have found that, as a process for producing an alkylene oxide adduct, a process in which a microflow reactor having a tubular flow passage with a specific inner diameter is used, a predetermined amount of alkylene oxide and a predetermined amount of an organic compound having an active hydrogen atom(s) are continuously supplied to the flow passage in a liquid state, and both are reacted under specific conditions while passing through the flow passage is properly suitable.

That is, the present invention relates to a process for producing an alkylene oxide adduct which comprises, in a process for producing an alkylene oxide adduct using a microflow reactor having a tubular flow passage, using a microflow reactor having a flow passage with an inner diameter of 0.05 to 3.5 mm, continuously supplying a predetermined amount of alkylene oxide and a predetermined amount of an organic compound having an active hydrogen atom(s) to the flow passage in a liquid state, and reacting these while passing through the same under conditions at a temperature of the flow passage of 70 to 200° C., and a pressure at a supplying port of the flow passage of 1 to 10 MPa. In addition, the present invention relates to an alkylene oxide adduct obtained by the process for producing such an alkylene oxide adduct.

The process for producing the alkylene oxide adduct according to the present invention (in the following, it is simply referred to as the production process of the present invention) is a process of obtaining an alkylene oxide adduct by using a specific microflow reactor, continuously supplying an alkylene oxide and an organic compound having an active hydrogen atom(s) to the flow passage in a liquid state, and reacting these while passing through the flow passage.

The microflow reactor to be used in the production process of the present invention is a reactor having a tubular flow passage, and the flow passage has an inner diameter of 0.05 to 3.5 mm, preferably 0.08 to 2.8 mm, more preferably 0.15 to 2.5 mm. In the production process of the present invention, a plural number of the microflow reactors may be used by connecting in series and/or parallel. All the plural number of the microflow reactors are not necessarily the reactors having a flow passage with the same inner diameter, and a reactor having a flow passage with a different inner diameter may be connected depending on the necessity within the range of the above-mentioned inner diameter. A length of the flow passage or a material of the constituting member of the respective microflow reactors, etc., can be optionally selected depending on a kind of the alkylene oxide adduct to be produced.

The alkylene oxide to be applied to the production process of the present invention may be mentioned ethylene oxide, propylene oxide, 1,2-butylene oxide, tetrahydrofuran, etc., and above all, ethylene oxide and/or propylene oxide is/are preferred.

The organic compound having an active hydrogen atom(s) to be applied to the production process of the present invention may be mentioned, 1) 1 to 6 equivalents of an aliphatic alcohol having 1 to 22 carbon atoms such as methyl alcohol, ethyl alcohol, propyl alcohol, butyl alcohol, pentyl alcohol, hexyl alcohol, heptyl alcohol, octyl alcohol, decyl alcohol, dodecyl alcohol, ethylene glycol, propylene glycol, butane diol, hexane diol, glycerin, trimethylol propane, sorbitol and pentaerythritol, etc., 2) 1 to 6 equivalents of an aliphatic alcohol having an ether group such as diethylene glycol, ethylene glycol monobutyl ether, diethylene glycol monobutyl ether, diglycerol, tetraethylene glycol, propylene glycol 1-monomethyl ether and tetrahydrofurfuryl alcohol, etc., 3) a monoalkylamine having 1 to 22 carbon atoms such as methylamine, ethylamine, propylamine, butylamine, pentylamine, hexylamine, heptylamine, octylamine, decylamine and dodecylamine, etc., 4) a dialkylamine having 1 to 22 carbon atoms such as dimethylamine, diethylamine, propyl methylamine, dibutylamine, pentylmethylamine, hexylmethylamine, octylmethylamine, dinonylamine, dilaurylamine, myristylmethylamine, dicetylamine, stearylmethylamine, arakynylmethylamine, 2-tetradecenylmethylamine, 2-pentadecenylmethylamine, 2-octadecenylmethylamine, 15-hexadecenylmethylamine, oleylmethylamine, linoleylmethylamine and eleostearylmethylamine, etc., 5) an alkanolamine having 1 to 3 hydroxyl groups in the molecule such as monoethanol-amine, monoisopropanolamine, diethanolamine, dipropanol-amine, triethanolamine and tri-isopropanolamine, etc., 6) an alkyl dialkanolamine and a dialkyl alkanolamine each having an alkyl group(s) with 1 to 18 carbon atoms such as diethylethanolamine, dibutylethanolamine, ethyl diethanolamine, butyl diethanolamine, stearyl diisopropanolamine, etc., 7) an alkoxylated polyamine having 1 to 5 hydroxyl groups in the molecule such as N-2-hydroxyethylaminoethyl-amine, N,N-di(2-hydroxyethyl)aminopropyl amine, N,N,N',N'-tetra(2-hydroxypropyl)-ethylenediamine and N,N-di(2-hydroxypropyl)-N'-2-hydroxypropyl-N'',N''-di(2-hydroxy-propyl)-diethylenetriamine, etc., 8) a hydroxycarboxylic acid having 1 to 5 hydroxyl groups in the molecule such as glycolic acid, lactic acid, malic acid, hydroxybutyric acid, hydroxystearic acid, tartaric acid, tetrahydroxysuccinic acid and gluconic acid, etc., 9) a fatty acid monoester of a divalent aliphatic alcohol obtained by 1 mol of a saturated or unsaturated aliphatic monocarboxylic acid having 6 to 18 carbon atoms such as hexanoic acid, octanoic acid, lauric acid, stearic acid, palmitoleic acid, oleic acid, etc., and 1 mol of ethylene glycol or butane diol, a fatty acid mono- or diester of a trivalent aliphatic alcohol obtained by 1 to 2 mol of the above-mentioned aliphatic monocarboxylic acid and 1 mol of glycerin or trimethylol propane, a fatty acid mono- to triester of a tetravalent aliphatic alcohol obtained by 1 to 3 mol of the above-mentioned aliphatic monocarboxylic acid and 1 mol of pentaerythritol, a fatty acid mono- to pentaester of a hexavalent aliphatic alcohol obtained by 1 to 5 mol of the above-mentioned aliphatic monocarboxylic acid and 1 mol of sorbitol and a partial ester obtained by the above-mentioned aliphatic monocarboxylic acid and sorbitan or sorbide, etc. Among these, the organic compound having an active hydrogen atom(s) is preferably a monovalent aliphatic alcohol having 1 to 6 carbon atoms, a divalent aliphatic alcohol having 1 to 4 carbon atoms, glycerin, diglycerin, pentaerythritol, a monoalkylamine having 1 to 6 carbon atoms and a dialkylamine having 1 to 6 carbon atoms, and more preferably a monovalent aliphatic alcohol having 1 to 6 carbon atoms and a monoalkylamine having 1 to 6 carbon atoms.

In the production process of the present invention, a catalyst is preferably used. Such a catalyst may be mentioned an alkali catalyst such as sodium hydroxide, potassium hydroxide, sodium alkoxide, potassium alkoxide, etc. Among these, sodium hydroxide, potassium hydroxide, sodium methoxide and potassium tertiary butoxide are preferred. Such a catalyst may be supplied to the flow passage of the microflow reactor separately from the alkylene oxide or the organic compound having an active hydrogen atom(s), or may be carried onto the flow passage, but it is preferred to supply it to the flow passage of the microflow reactor after mixing with the organic compound having an active hydrogen atom(s).

In the production process of the present invention, a predetermined amount of an alkylene oxide and a predetermined amount of an organic compound having an active hydrogen atom(s), and further a predetermined amount of a catalyst are continuously supplied to the flow passage of the microflow reactor in a liquid state, and these reactants are reacted while passing through the flow passage under the conditions of a temperature of the flow passage of 70 to 200° C., preferably 80 to 180° C., and a pressure at the supply port of the flow passage of 1 to 10 MPa, preferably 1.5 to 5 MPa, generally for 0.5 to 600 minutes, preferably 1 to 200 minutes.

In the production process of the present invention, it is preferred that a material in which the alkylene oxide and the organic compound having an active hydrogen atom(s), and further the catalyst are mixed by using a mixer is supplied to the microflow reactor. Above all, it preferably has two or more independent supply routes and one discharge route (liquid feeding route) connected to a confluence part of these supply routes, a liquid alkylene oxide is supplied from one supply route, an organic compound having an active hydrogen atom(s) from another supply route and further a catalyst in a liquid state into the mixer, and a mixed material in the mixer is discharged to supply into a microflow reactor. Such a mixer may be mentioned a micro mixer.

The micro mixer is preferably a mixer having inner diameters of the supply route and the discharge route of 0.01 to 3.5 mm, more preferably 0.01 to 1.5 mm, and particularly preferably 0.04 to 0.8 mm. Cross-sectional shapes of the supply route and the discharge route are not particularly limited, and can be optionally selected depending on the purposes.

A micro mixer having two supply routes may be mentioned a T-shaped micro mixer, a Y-shaped micro mixer, etc. Also, a mixer having three supply routes may be mentioned a cruciform micro mixer, etc.

As the micro mixer explained above, a commercially available product can be utilized, and may be mentioned, for example, Single mixer and Caterpillar Split Recombine Micro Mixer, both trade names, manufactured by Institute für Mikrotechnik Mainz GmbH (IMM), microglass reactor, trade name, manufactured by Microglass Co., Ltd., CYTOS, trade name, manufactured by CPC system Co., Ltd., YM-1 type mixer and YM-2 type mixer, both trade names, manufactured by Yamatake Corporation, Mixing tee, trade name, manufactured by Shimadzu GLC Ltd., IMT chip reactor, trade name, manufactured by Institute of Microchemical Technology Co., Ltd., Micro High—Mixer, trade name, manufactured by TORAY ENGINEERING CO., LTD., Union tee, trade name, manufactured by Swagelok Company, etc.

A method for supplying the alkylene oxide, the organic compound having an active hydrogen atom(s), and further the alkali catalyst to the supply route of the micro mixer in a liquid state is not particularly limited. For example, the organic compound having an active hydrogen atom(s) and the alkali catalyst are provisionally mixed, and the mixed solution can be supplied to the supply route of the micro mixer.

In the production process of the present invention, depending on the purpose, devices such as a fluid feeding device, a liquid amount controller, a storage container, a reservoir, a temperature adjusting device, a sensor device, etc., may be optionally provided and used.

Effects of the Invention

According to the present invention, there are effects that the alkylene oxide adduct can be continuously produced with an optional size from a small size to a large size, a temperature and a pressure at the time of the addition reaction can be controlled with high precision, and as a result, the alkylene oxide adduct with high quality having no coloring and narrow molecular weight distribution can be continuously produced, and the above can be accomplished simultaneously.

In the following, Examples, etc., are mentioned to show more specifically the constitution and the effects of the present invention, but the present invention is not limited by these Examples. Incidentally, in the following Examples and Comparative examples, all part means part by mass, and all % means % by mass.

EXAMPLES

Test Division 1 (Production of Alkylene Oxide Adduct)

Example 1

As a supply port of a microflow reactor, an apparatus in which a T-shaped micro mixer to which a discharge port (liquid feeding port) had been connected was used. Ethylene oxide was continuously supplied with a fixed quantity to the first supply route (an inner diameter: 0.2 mm) of the T-shaped micro mixer and a mixed solution of methyl alcohol and sodium methoxide was continuously supplied with a fixed quantity to the second supply route (inner diameter: 0.2 mm) simultaneously, whereby ethylene oxide, methyl alcohol and sodium methoxide are joined at the discharge route (inner diameter: 0.2 mm) of the T-shaped micro mixer and mixed. Subsequently, the liquid state mixture was continuously supplied with a fixed quantity from the discharge port of the T-shaped micro mixer to the tubular flow passage (made of SUS316, inner diameter: 1 mm, length: 20 m) through the supply port of the microflow reactor, and reacted under the conditions of a temperature of the tubular flow passage of the microflow reactor of 90° C. and a pressure at the supply port of 2.6 MPa while passing through the flow passage for 20 minutes to obtain an alkylene oxide adduct.

Examples 2 to 12

In the same manner as in Example 1, alkylene oxide adducts of the respective Examples were obtained using the specification of the apparatus and under the reaction conditions mentioned in Table 1.

Comparative Example 1

In the same manner as in Example 1, an alkylene oxide adduct was obtained. The specification of the apparatus and the reaction conditions are as shown in Table 1, and a flow reactor having a flow passage with an inner diameter of 81 mm was herein used and the reaction was carried out under the condition of a pressure of the supply port of 0.4 MPa.

Comparative Example 2

Into an autoclave made of stainless having an inner volume of 2 L were charged 100 g of methyl alcohol and 4 g of sodium methoxide, and after replacing inside the autoclave with nitrogen three times, 1330 g of a mixture of ethylene oxide/propylene oxide=43/57 (mass ratio) was introduced therein over 2 hours under the condition of a temperature at 90° C., during which the temperature was raised to 140° C. Ripening was further carried out for one hour to complete the reaction. The reaction system was cooled to room temperature, the remaining minute amounts of the ethylene oxide and the propylene oxide were removed under reduced pressure to obtain an alkylene oxide adduct.

Comparative Example 3

Into an autoclave made of stainless having an inner volume of 10 L were charged 600 g of methyl alcohol and 24.4 g of sodium methoxide, and after replacing inside the autoclave with nitrogen three times, when 7,425 g of ethylene oxide were introduced therein over 2 hours under the condition at a temperature of 90° C., then, an abnormal reaction occurred accompanied by abrupt temperature-raising and pressure-raising, so that the reaction was stopped and ripening was further carried out for one hour to obtain an alkylene oxide adduct.

Specification of the apparatus used in the above-mentioned respective examples and reaction conditions, etc., were shown in Table 1 all together.

TABLE 1

| | T-shaped micro mixer | | | | | | | |
| --- | --- | --- | --- | --- | --- | --- | --- | --- |
| | First supply route | | | Second supply route | | | | |
| Division | Inner diameter (mm) | Kind of AO | Supply of AO (g/min) | Inner diameter (mm) | Kind of M | Kind of CA | CA/M (mass ratio) | Supply of CA + M (g/min) |
| Example | | | | | | | | |
| 1 | 0.2 | AO-1 | 0.65 | 0.2 | M-1 | CA-1 | 4.06 | 0.05 |
| 2 | 0.1 | AO-2 | 0.27 | 0.1 | M-2 | CA-3 | 1.62 | 0.02 |
| 3 | 0.2 | AO-1 | 0.22 | 0.2 | M-3 | CA-2 | 4.07 | 0.02 |
| 4 | 0.08 | AO-2 | 0.64 | 0.08 | M-4 | CA-4 | 2.26 | 0.06 |
| 5 | 0.07 | AO-1 | 0.61 | 0.07 | M-5 | CA-2 | 0.33 | 0.14 |
| 6 | 0.2 | AO-1 | 0.09 | 0.2 | M-1 | CA-1 | 0.31 | 0.02 |
| 7 | 0.4 | AO-2 | 0.03 | 0.6 | M-5 | CA-3 | 0.43 | 0.03 |

TABLE 1-continued

| Division | | | | | | | | |
|---|---|---|---|---|---|---|---|---|
| 8 | 0.4 | AO-1 | 0.66 | 0.03 | M-1 | CA-4 | 7.19 | 0.04 |
| 9 | 0.6 | AO-1 | 1.03 | 0.6 | M-2 | CA-1 | 2.43 | 0.14 |
| 10 | 0.6 | AO-2 | 0.10 | 0.6 | M-2 | CA-3 | 1.49 | 0.01 |
| 11 | 1 | AO-1 | 0.35 | 1 | M-1 | CA-1 | 8.75 | 0.01 |
| 12 | 2 | AO-1 | 0.75 | 2 | M-5 | CA-1 | 1.20 | 0.14 |
| Comparative example | | | | | | | | |
| 1 | 9 | AO-1 | 11950 | 13 | M-1 | CA-1 | 4.06 | 900 |
| 2 | *2 | AO-2 | — | *2 | M-1 | CA-1 | 4.06 | — |
| 3 | *3 | AO-1 | — | *3 | M-1 | CA-1 | 4.06 | — |

| | T-shaped micro mixer Discharge route (liquid feeding route) | | Flow passage of microflow reactor | | | | Pressure at supply port (MPa) |
|---|---|---|---|---|---|---|---|
| Division | Inner diameter (mm) | Flow amount (g/min) | Inner diameter (mm) | Length (m) | Retention time (min) | Temperature (° C.) | |
| Example | | | | | | | |
| 1 | 0.2 | 0.70 | 1 | 20 | 20 | 90 | 2 |
| 2 | 0.07 | 0.29 | 1 + 2 | 10 + 4 | 60 | 140 | 3 |
| 3 | 0.15 | 0.23 | 0.5 | 40 | 30 | 120 | 2.5 |
| 4 | 0.08 | 0.71 | 0.25 + 0.5 + 1 + 2 | 10 + 20 + 20 + 4 | 40 | 160 | 5 |
| 5 | 0.07 | 0.75 | 1 | 30 | 30 | 100 | 4 |
| 6 | 0.15 | 0.11 | 0.1 | 80 | 5 | 80 | 8 |
| 7 | 0.4 | 0.05 | 2 | 1 | 60 | 90 | 1.4 |
| 8 | 0.4 | 0.70 | 1 | 20 | 20 | 90 | 3.4 |
| 9 | 1 | 1.17 | 1 | 50 | 30 | 120 | 2.9 |
| 10 | 1 | 0.11 | 1 | 10 | 60 | 140 | 3.5 |
| 11 | 1 | 0.35 | 1 + 2 | 20 + 10 | 120 | 140 | 4 |
| 12 | 2 | 0.89 | 1 + 2 + 3 | 1 + 2 + 3 | 30 | 100 | 2 |
| Comparative example | | | | | | | |
| 1 | 81 | 12850 | 81 | 67 | 24 | 120 | 0.4 |
| 2 | *2 | — | *2 | *2 | *2 | 90-140 | 0.5 |
| 3 | *3 | — | *3 | *3 | *3 | 90-140 | 0.9 |

In Table 1,
AO: Alkylene oxide
AO-1: Ethylene oxide
AO-2: Ethylene oxide/propylene oxide=43/57(mass ratio)
M: Organic compound having active hydrogen atom(s)
M-1: Methyl alcohol
M-2: Normal butyl alcohol
M-3: Propylamine
M-4: Diethylene glycol
M-5: Glycerin
CA: Alkali catalyst
CA-1: Sodium methoxide
CA-2: Sodium hydroxide
CA-3: Potassium hydroxide
CA-4: Potassium tertiary butoxide Inner diameter and length of flow passage of microflow reactor: when a plural number of microflow reactors having different diameter of flow passage were connected, for example, from the micro mixer side, when a microflow reactor having a flow passage with an inner diameter of 0.5 mm and a length of 10 m and a microflow reactor having a flow passage with an inner diameter of 1 mm and a length of 20 m were connected, the inner diameter was shown by 0.5+1, and the length was shown by 10+20.

*2: As mentioned above, the conditions where the reaction was carried out by using an autoclave made of stainless having an inner volume of 2 L (a supply port pressure is the maximum pressure in the autoclave).

*3: As mentioned above, the conditions where the reaction was carried out by using an autoclave made of stainless having an inner volume of 10 L (a supply port pressure is the maximum reached pressure in the autoclave, actually the safety valve which acts with 0.9 MPa in the reaction opened 4 times).

The above are the same as in Table 2.

Test Division 2 (Physical Property of Produced Alkylene Oxide Adduct)

With regard to the alkylene oxide adducts produced in the respective examples of Test division 1, AO/M (mass ratio), M/EO/PO (molar ratio and mass ratio, EO is ethylene oxide and PO is propylene oxide) were obtained. Also, color hue was evaluated by the following standard. Further, a ratio of Mw/Mn was obtained by the following mentioned method. The results were shown in Table 2 all together.

Evaluation of Color Hue

Color hue was evaluated based on JIS-K0071-1: 1998 (Testing Method for Colour of Chemical Products-Part I: Hazen unit color number (platinum-cobalt scale)) according to the following standard.

⊚: It corresponds to 0 to 20 with a number of the standard matching solution

◯: It corresponds to 30 to 50 with a number of the standard matching solution

Δ: It corresponds to 60 to 150 with a number of the standard matching solution

×: It corresponds to 200 or more with a number of the standard matching solution Mw: Weight average molecular weight in terms of polystyrene by GPC (gel permeation chromatography)

Mn: Number average molecular weight in terms of polystyrene by GPC (gel permeation chromatography)

TABLE 2

| Division | | AO/M (wt) | M/EO/PO (molar ratio) | M/EO/PO (mass ratio) | Color hue | Mw/Mn |
|---|---|---|---|---|---|---|
| Example | 1 | 13.3 | 1/9/0 | 7/93/0 | ⊚ | 1.1 |
| | 2 | 13.3 | 1/11/11 | 7/41/52 | ⊚ | 1.1 |
| | 3 | 13.3 | 1/17/0 | 7/93/0 | ⊚ | 1.1 |
| | 4 | 10.1 | 1/11/11 | 9/40/51 | ⊚ | 1.1 |
| | 5 | 4.3 | 1/10/0 | 17/83/0 | ⊚ | 1.1 |
| | 6 | 4.0 | 1/3/0 | 20/80/0 | ○ | 1.1 |
| | 7 | 1.1 | 1/1/1 | 48/23/29 | ⊚ | 1.2 |
| | 8 | 15.7 | 1/12/0 | 6/94/0 | ○ | 1.2 |
| | 9 | 7.3 | 1/12/0 | 12/88/0 | ○ | 1.2 |
| | 10 | 13.3 | 1/10/10 | 7/41/52 | ○ | 1.2 |
| | 11 | 49.0 | 1/32/0 | 2/98/0 | ○ | 1.3 |
| | 12 | 5.3 | 1/5/5 | 16/37/47 | ○ | 1.3 |
| Comparative example | 1 | 13.3 | 1/9/0 | 7/93/0 | Δ | 1.3 |
| | 2 | 13.3 | 1/4/4 | 7/41/52 | X | 1.3 |
| | 3 | 13.3 | 1/9/0 | 7/93/0 | X | 1.2 |

As can be seen from the results shown in Table 2, according to the production process of the present invention, a high quality alkylene oxide adduct without coloring and narrow molecular weight distribution can be continuously produced.

The invention claimed is:

1. A process for producing an alkylene oxide adduct, comprising:
   using a microflow reactor having a tubular flow passage and a micromixer connected to a supply port of the microflow reactor, wherein an apparatus having a flow passage with an inner diameter of 0.15 to 2.5 mm and a length of at least 10 m is used as the microflow reactor, and an apparatus having two or more independent supply routes and a discharge route connected to a confluence part of the supply routes and having inner diameters of the supply routes and the discharge route of 0.07 to 0.2 mm is used as the micromixer,
   supplying a liquid alkylene oxide reactant to a first supply route of the micromixer,
   supplying an organic compound reactant having an active hydrogen atom(s) and an alkaline catalyst reactant in a liquid state to a second supply route into the micromixer, and
   discharging a mixed material mixed in the micromixer from the discharge route of the micromixer into the flow passage of the microflow reactor via the supply port of the microflow reactor,
   wherein the reactants are reacted while passing through the microflow reactor under conditions of a temperature of the flow passage of the microflow reactor of 70 to 200° C., a pressure at a supply port of the flow passage of 1 to 10 MPa, and with a retention time in the flow passage of at least 20 minutes, to produce an alkylene oxide adduct having a platinum-cobalt scale number of between 0 and 20 and a Mw/Mn ratio of no more than 1.1.

2. The production process of the alkylene oxide adduct according to claim 1, wherein the alkylene oxide is ethylene oxide and/or propylene oxide.

3. The production process of the alkylene oxide adduct according to claim 2, wherein the organic compound having an active hydrogen atom(s) is one or two or more selected from a monovalent aliphatic alcohol having 1 to 6 carbon atoms and a monoalkylamine having 1 to 6 carbon atoms.

4. The production process of the alkylene oxide adduct according to claim 1, wherein the alkylene oxide reactant is ethylene oxide, the organic compound having an active hydrogen atom(s) reactant is methyl alcohol, and the alkaline catalyst reactant is sodium methoxide.

5. The production process of the alkylene oxide adduct according to claim 1, wherein the conditions of the tubular flow passage of the microflow reactor are a temperature of 90 to 160° C. and a pressure at the supply port of 2 to 5 MPa, while passing through the flow passage for 20 to 60 minutes to obtain an alkylene oxide adduct.

* * * * *